(12) United States Patent
Dent et al.

(10) Patent No.: US 9,584,772 B2
(45) Date of Patent: Feb. 28, 2017

(54) METHOD AND APPARATUS FOR INSPECTING PARTS

(71) Applicant: Inspect 100 Ltd., Canton, OH (US)

(72) Inventors: William Dennis Dent, Canton, OH (US); Bryan Earl Emary, Lake Orion, MI (US)

(73) Assignee: INSPECT 100 LTD, Anton, OH (US)

( * ) Notice: Subject to any disclaimer, the term of this patent is extended or adjusted under 35 U.S.C. 154(b) by 226 days.

(21) Appl. No.: 14/266,914

(22) Filed: May 1, 2014

(65) Prior Publication Data

US 2015/0317782 A1   Nov. 5, 2015

(51) Int. Cl.
*G06T 7/00* (2006.01)
*H04N 7/18* (2006.01)
*B07C 5/02* (2006.01)
*B65B 43/26* (2006.01)

(52) U.S. Cl.
CPC ............ *H04N 7/183* (2013.01); *G06T 7/0004* (2013.01); *H04N 7/181* (2013.01)

(58) Field of Classification Search
CPC .............................. H04N 7/181; G06T 7/0004
USPC ......................................................... 348/125
See application file for complete search history.

(56) References Cited

U.S. PATENT DOCUMENTS

| 3,782,542 | A | | 1/1974 | Scribner |
| 4,172,524 | A | * | 10/1979 | Holm ................... B07C 5/3408 |
| | | | | 209/524 |
| 4,497,409 | A | | 2/1985 | Chong |
| 4,619,141 | A | | 10/1986 | Yoshieda et al. |
| 5,755,335 | A | * | 5/1998 | Michelotti ........... B07C 5/3412 |
| | | | | 198/394 |
| 2012/0020526 | A1 | | 1/2012 | Teti et al. |

FOREIGN PATENT DOCUMENTS

EP          1795883          6/2007

* cited by examiner

*Primary Examiner* — Hee-Yong Kim
(74) *Attorney, Agent, or Firm* — Hudak, Shunk & Farine Co. LPA

(57) ABSTRACT

The method and apparatus for inspecting parts generally includes three main components: an indexer assembly, a clamp assembly, and a camera system. The indexer assembly is configured to rotate parts individually into proximity to the clamp assembly. The clamp assembly is configured to clamp the part and move the part into proximity to the camera system. The clamp assembly may be comprised of a first portion and a second portion which are independently moveable with respect to one another. The camera system is configured to scan the part as the clamp assembly moves the part past and create an image thereof. The camera system is further configured to analyze the image to inspect the part.

17 Claims, 17 Drawing Sheets

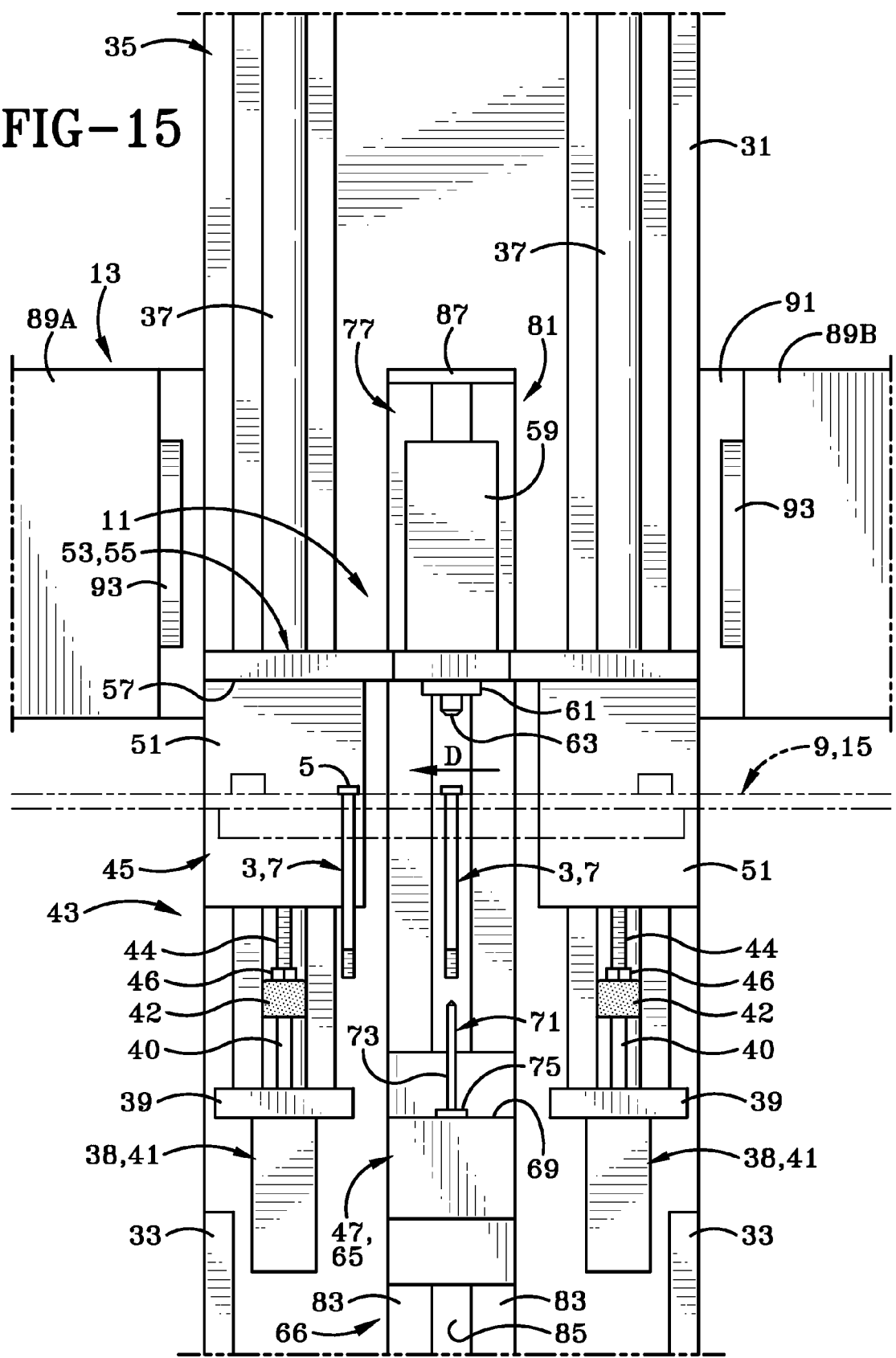

METHOD AND APPARATUS FOR INSPECTING PARTS

BACKGROUND OF THE INVENTION

1. Technical Field

The present invention relates to inspecting manufactured parts for defects or undesirable qualities. More particularly, the present invention relates to mechanically moving a part past a camera for automated inspection of the part. Specifically, the present invention relates to clamping a part to be inspected between a first portion and a second portion of a clamp and thereafter moving the part via the clamp past a line scan camera to inspect the part.

2. Background Information

Common everyday parts such as off-the-shelf screws, bolts, and other fasteners are relatively inexpensive and easily located. These off-the-shelf parts are purposely relatively low quality as these parts are used in home improvement projects, woodworking, or other common activities where quality isn't a major concern. Conversely, when these parts such as custom made screws or bolts are used in mission critical systems such as in the aerospace field, every part needs to be exact and pass rigorous testing and inspection. Failure of the mission critical part due to a flaw in the material or shape may be catastrophic. Often these mission critical parts are made in a low production run of a specific size part to fit a specific need. Inasmuch as the size and shape of these mission critical parts are always changing to fit the production run, inspecting each part is primarily done one part at a time by manually reviewing the part with the naked eye or a microscope. This is very time consuming and expensive, increasing the cost of each part to the end purchaser. Thus, there exists a tremendous need in the art to automate the scanning of mission critical parts and provide an apparatus and method for automatically inspecting parts in bulk.

BRIEF SUMMARY OF THE INVENTION

In one aspect, the invention may provide an apparatus adapted to inspect a part, the apparatus comprising: a clamp having a first portion and a second portion, wherein the first portion and the second portion are independently movable to clamp the part therebetween and move the part along a path; a first camera, wherein the first camera is configured to capture a first image of the part as the clamp moves the part along the path; and a plate defining a slot for receiving the part therein, wherein the plate is rotatable to selectively dispose the part between the first portion and the second portion and remove the part from between the first portion and the second portion.

In another aspect, the invention may provide a method for inspecting parts, the method comprising the steps of: clamping a part to be inspected; moving the clamp and the part past a camera; using the camera to form an image of the part; and analyzing the image to inspect the part.

BRIEF DESCRIPTION OF THE SEVERAL VIEWS OF THE DRAWINGS

One or more preferred embodiments that illustrate the best mode(s) are set forth in the drawings and in the following description. The appended claims particularly and distinctly point out and set forth the invention.

The accompanying drawings, which are incorporated in and constitute a part of the specification, illustrate various example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 15 is a similar view thereof with the plate rotating the original bolt away from the clamp assembly and rotating a new bolt into the clamp assembly.

Similar numbers refer to similar parts throughout the drawings.

DETAILED DESCRIPTION OF THE INVENTION

Figure 1:
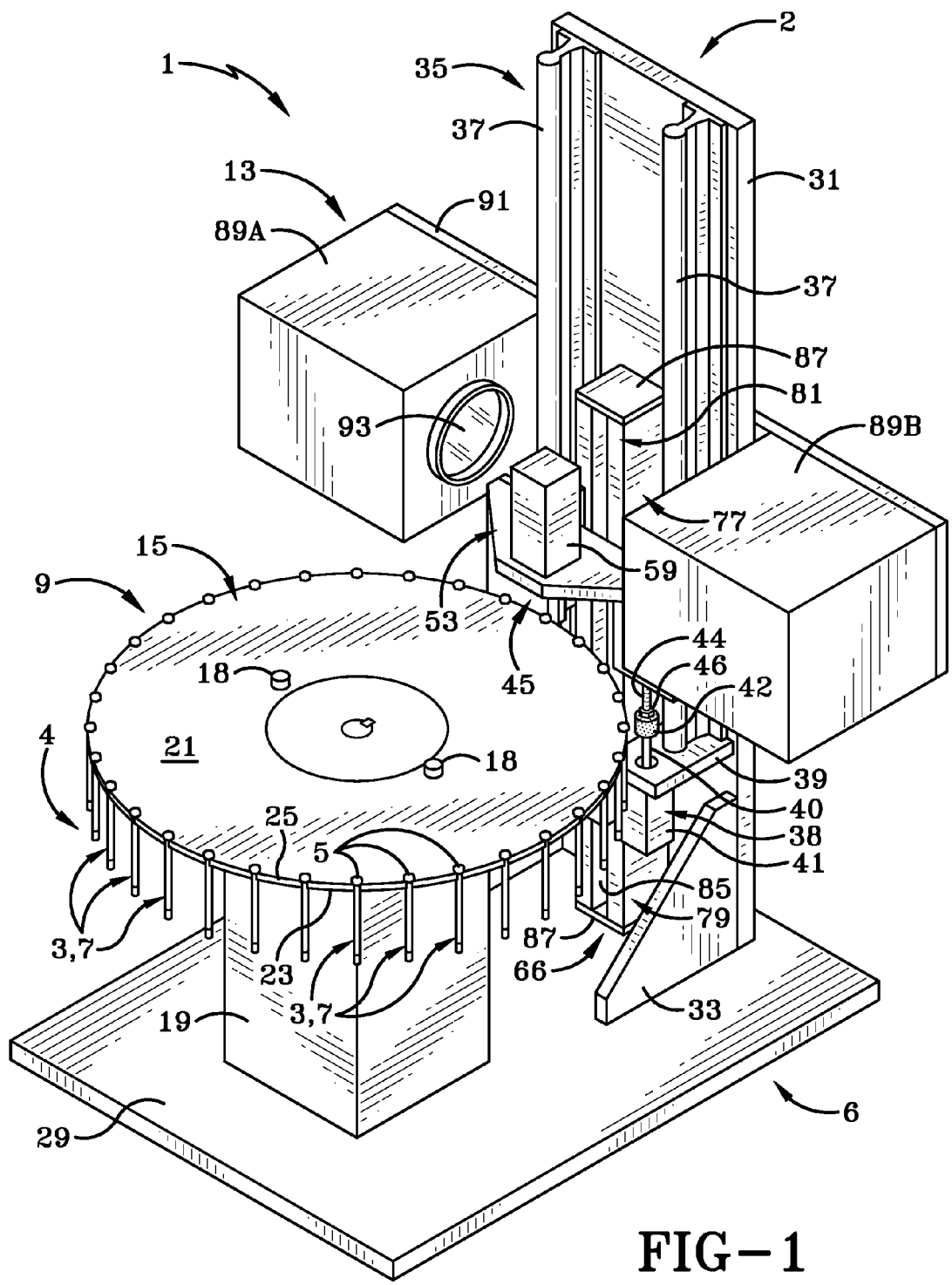
FIG. 1 is a perspective view of an apparatus for inspecting parts and showing the clamp assembly, indexer assembly, and the camera system.

An apparatus for inspecting a part is shown in FIGS. 1-15 and referred to generally herein as apparatus 1. While apparatus 1 may be directed primarily to inspecting a part, the present invention embodies using apparatus 1 for measuring or cataloging a part, or any other general observational type of interaction with apparatus 1 and a part. For exemplary purposes, a part 3 is shown in a general bolt shape, and will hereinafter be referred to as bolt 3. As commonly understood in the art, the typical bolt shape embodied by bolt 3 includes a head 5 having a particular cross-sectional area and a shaft 7 extending therefrom and having a smaller cross-sectional area. Head 5 is disposed at a first end of bolt 3 while shaft 7 extends from head 5 to the second end of bolt 3.

Figure 6:
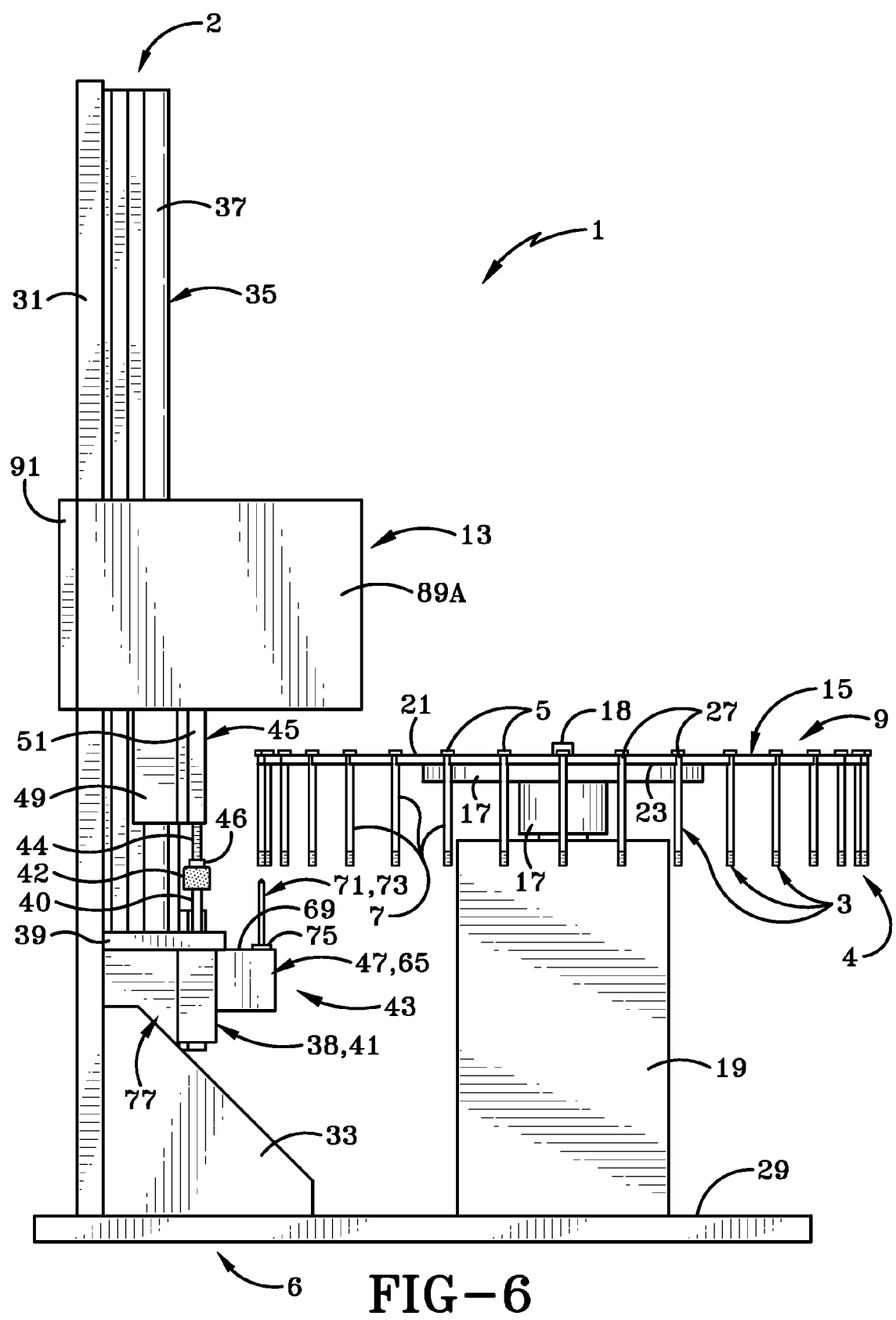
FIG. 6 is a left side elevational view thereof.

As shown in FIGS. 1-4, apparatus 1 extends from a top end 2 (FIG. 2) to a bottom end 6 (FIG. 2) and broadly includes three main components, an indexer assembly 9, a clamp assembly 11, and a camera system 13. As shown in FIG. 6, these three components broadly work in conjunction to inspect a plurality of bolts 3 by rotating each bolt 3 with indexer assembly 9 into proximity with clamp assembly 11. Clamp assembly 11 thereafter clamps onto a particular bolt 3 and moves bolt 3 out of indexer assembly 9 and along a path and into proximity with camera system 13 for inspection. After inspection, clamp assembly 11 moves bolt 3 back into indexer assembly 9 and releases the clamp. Thereafter, indexer assembly 9 indexes to the next bolt 3 in the plurality for the next inspection.

As shown in FIGS. 1-4, indexer assembly 9 includes a plate 15 removably secured to a brace 17 by a plurality of fasteners 18. Brace 17 is rotatably secured to a motor (not shown) disposed in a housing 19. The motor provides rotational axial movement to brace 17 which transfers this movement to plate 15. Plate 15 includes a upper surface 21, a lower surface 23, and a perimeter surface 25 extending therebetween. Plate 15 defines a plurality of slots 27, wherein each slot 27 is correspondingly sized to receive bolt 3 therein. Slots 27 open through perimeter surface 25 to allow for a sliding reception of bolt 3 therethrough. As shown in FIGS. 5 and 6, blot 3 slides into slot 27 in the direction of Arrow A and is gravitationally frictionally engaged with plate 15 by way of head 5 resting on upper surface 21. Thus, slots 27 are larger than shaft 7 in order to receive bolt 3 therein, yet smaller than head 5 to ensure bolt 3 doesn't fall through slot 27 once bolt 3 is placed in slot 27.

Figure 1A:
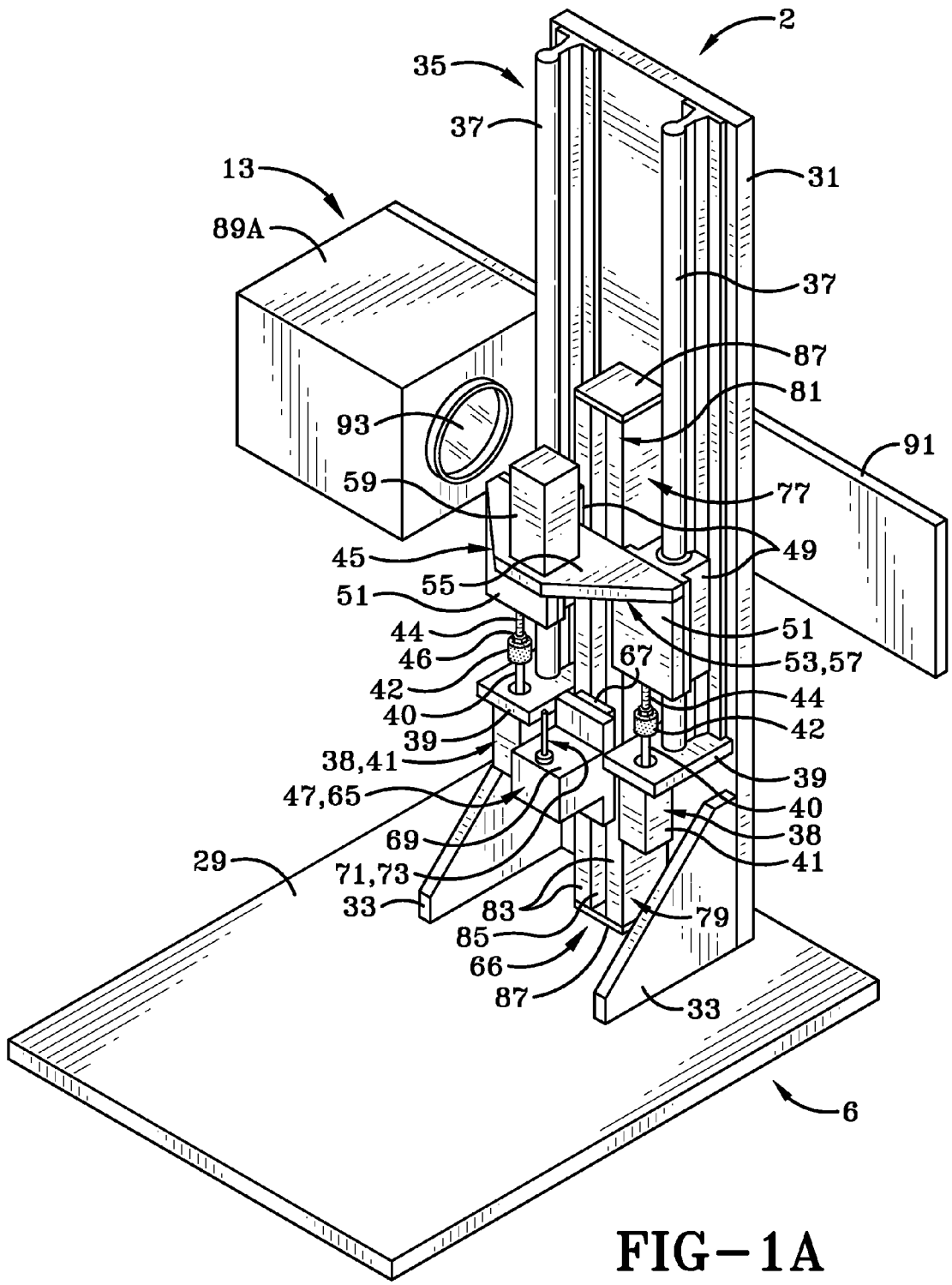
FIG. 1A is a similar view thereof, with an indexer assembly removed for a clearer view of the remaining features.

As shown in FIG. 1A, housing 19 rests on a plate 29 or may be alternatively configured to rest directly on a floor or another surface. A back wall 31 extends upwardly from plate 29 and is braced by a pair of brace walls 33 extending from the intersection of plate 29 and back wall 31. While plate 29, back wall 31, and brace walls 33 are shown, it will be readily understood that the overall framework of apparatus 1 may be altered or configured in any way without changing the overall novelty of apparatus 1. For example, housing 19 may be disposed or secured in a more horizontal orientation, rather than the vertical orientation shown in FIG. 1A. Brace walls 33 may be omitted altogether or formed in a different shape or extended between plate 29 and back wall 31 in another position on apparatus 1. Back wall 31 may be provided by a wall of a structure, such as a warehouse or manufacturing facility. As such, any configuration of plate 29, back wall 31, and brace walls 33 are contemplated and encompassed by the present invention.

Figure 2:
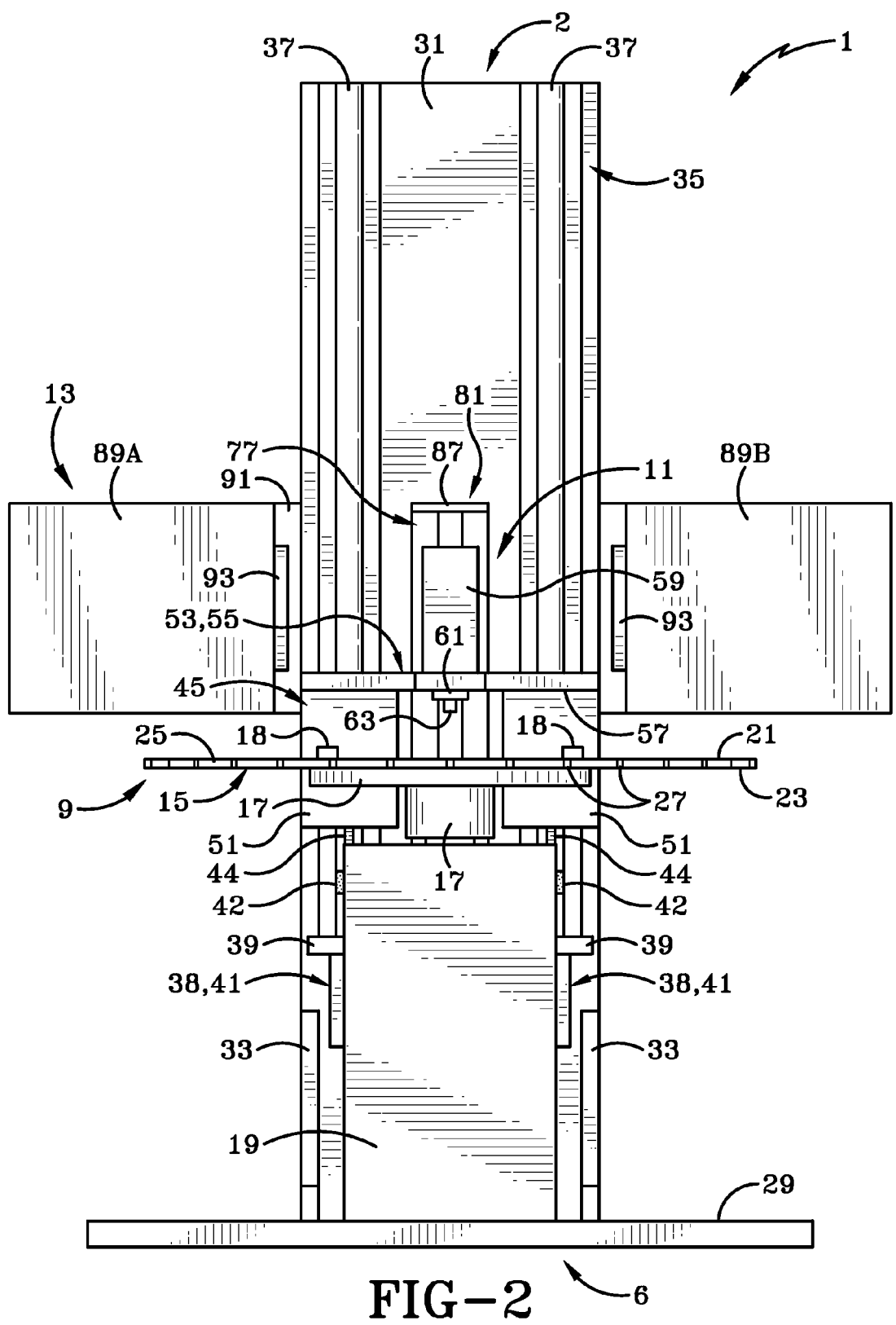
FIG. 2 is a front elevational view of the apparatus for inspecting parts.
Figure 2A:
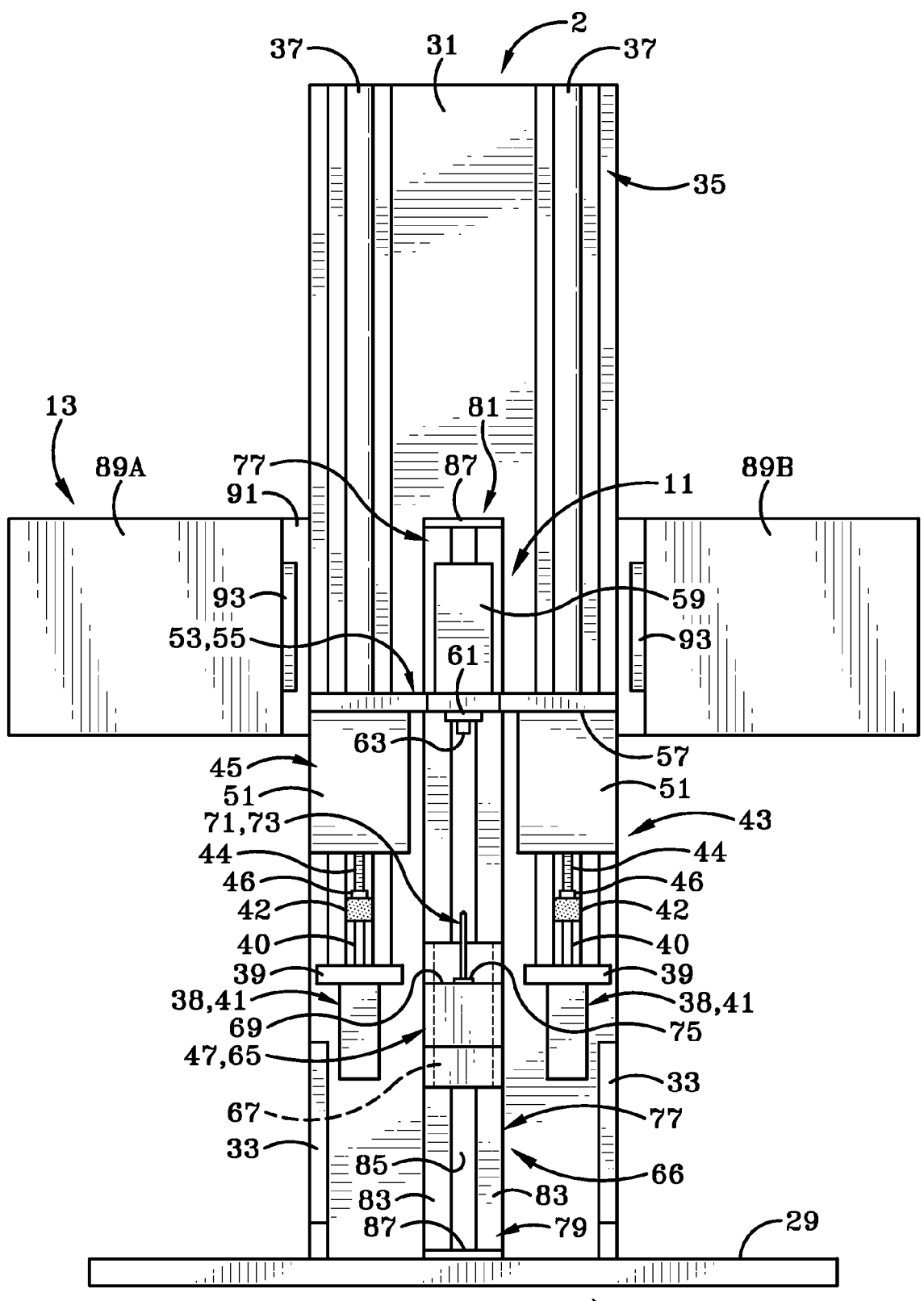
FIG. 2A is a similar view thereof, with the indexer assembly removed for a clearer view of the remaining features.

As shown in FIGS. 1A and 2A, clamp assembly 11 includes a track 35 having a pair of spaced apart rails 37 is secured to back wall 31, whereby each rail 37 extends generally from top end 2 to a shelf 39 positioned generally where brace walls 33 meet back wall 31. Each shelf 39 is buttressed by a housing 41 to provide stabilization for the corresponding shelf 39 and rail 37. Each housing 41 also encloses a portion of a piston assembly 38, which may be embodied by a pneumatic or hydraulic piston assembly. Piston assembly 38 includes a cylinder (not shown) which contains a piston (not shown) slidably disposed in the cylinder. Piston assembly 38 further includes a piston rod 40 connected to the piston at one end and extending through a hole defined by shelf 39 to be secured to a bumper 42 at the opposite end. As such, hydraulic or pneumatic actuation of piston inside cylinder moves piston rod 40 and bumper 42. Bumper 42 is a rubberized stopper mechanism which abuts shelf 39 when piston rod 40 is in the lowered position and is spaced apart from shelf 39 when piston rod 40 is in the raised position.

Figure 3:
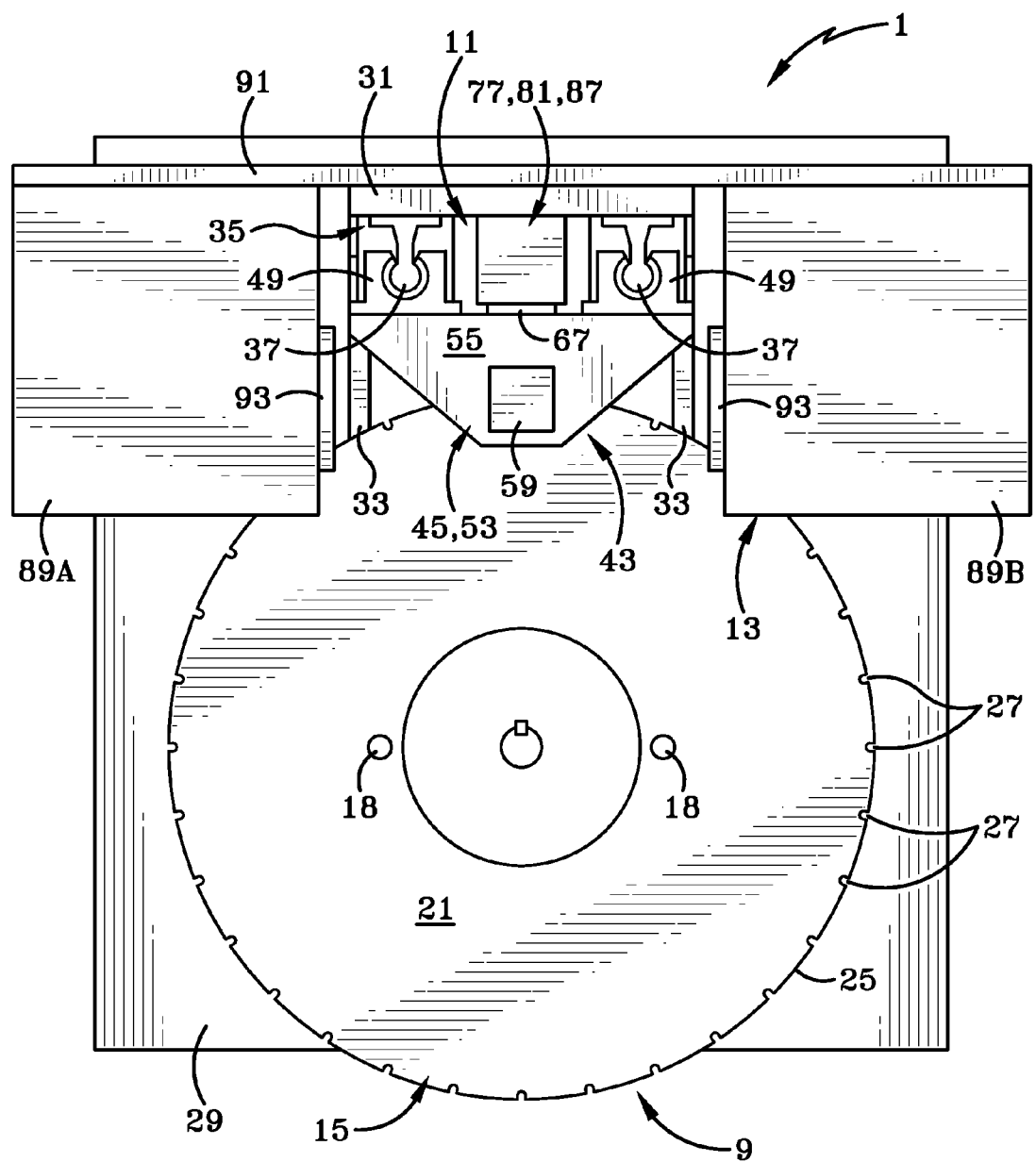
FIG. 3 is a top view of the apparatus for inspecting parts.
Figure 7:
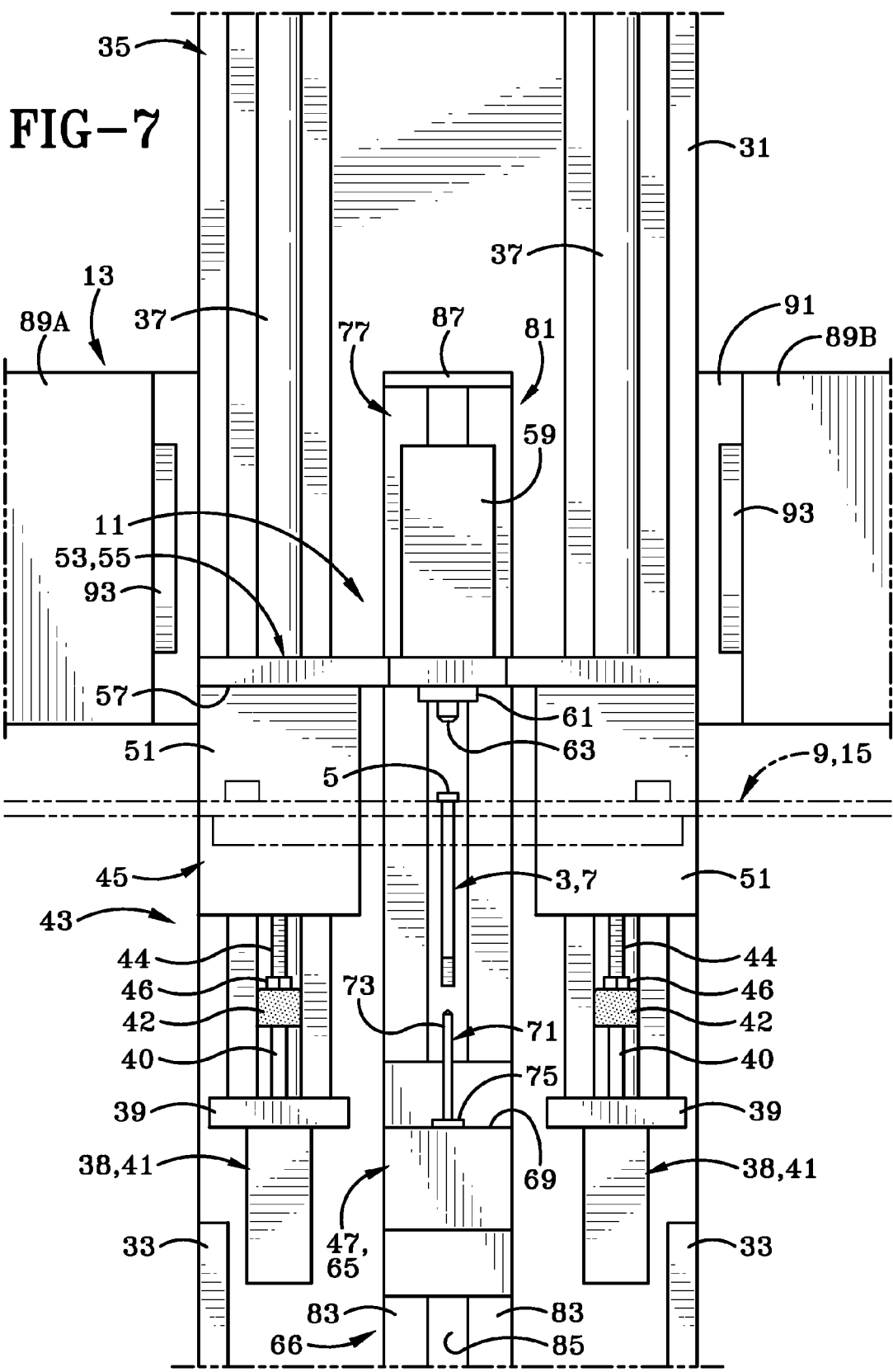
FIG. 7 is an enlarged front elevational view of the apparatus for inspecting parts with the plate shown in phantom.

As shown in FIGS. 1A and 2A, clamp assembly 11 further includes a clamp 43 comprised of a first portion 45 clampably engageable with a second portion 47. First portion 45 and second portion 47 are independently movable to selectively clamp bolt 3 therebetween. First portion 45 generally resembles a carriage that rides along track 35. As shown in FIG. 3, first portion 45 includes a pair of jaws 49, whereby each jaw 49 connects to one of the rails 37 to hold first portion 45 slidably thereto. A spacer 51 is secured to each jaw 49 to provide an area to secure a shelf 53 thereto. Shelf 53 is a flat structure that extends generally horizontally and includes an upper surface 55 and a lower surface 57. A weight 59 is secured to upper surface 55 of shelf 53 to increase the downward force on shelf 53 and increase the overall weight of first portion 45. As shown in FIG. 7, a spacer 61 is secured to lower surface 57 of shelf 53 to provide a surface for securing a pressure head 63.

Figure 4:
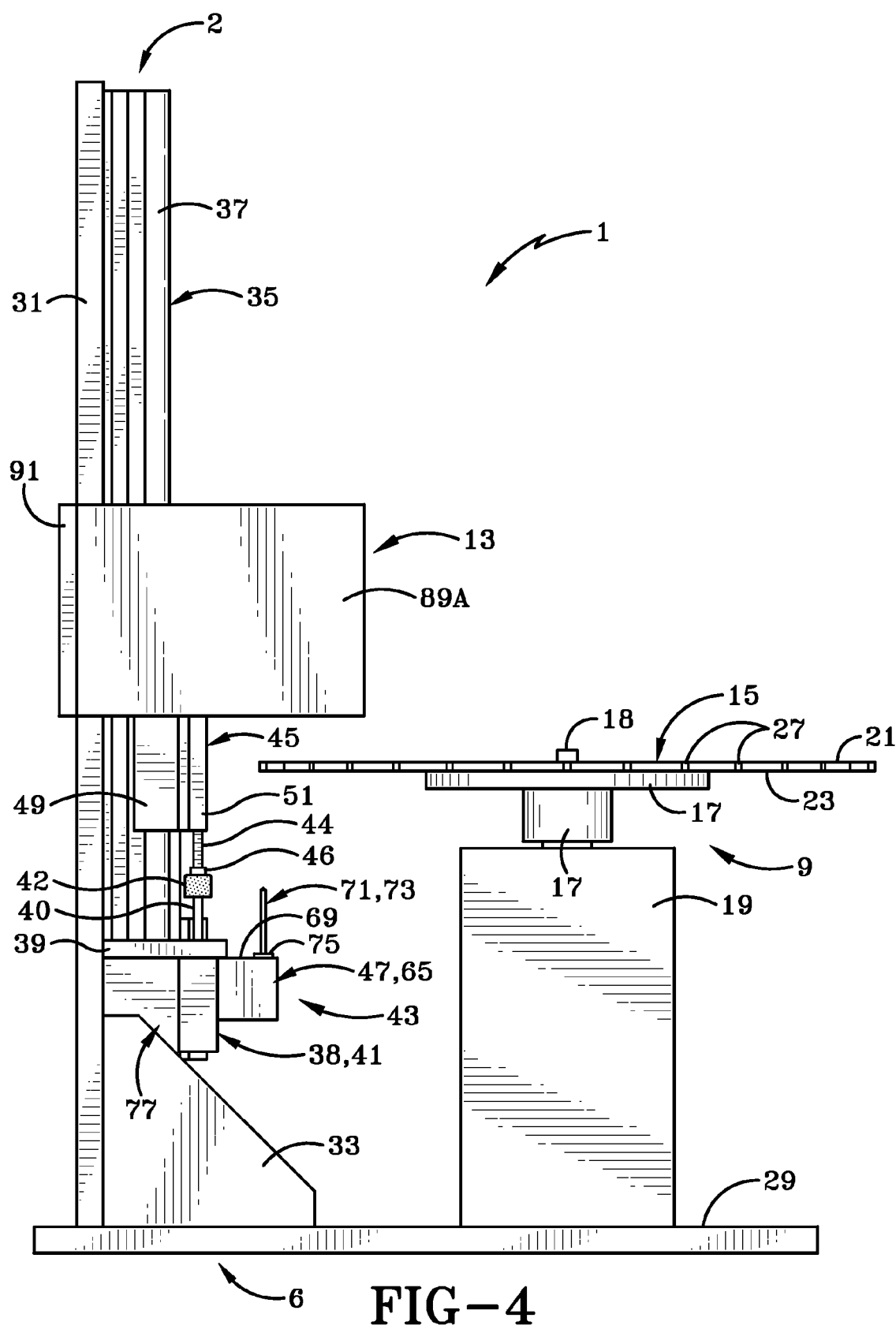
FIG. 4 is a left side elevational view thereof.
Figure 5:
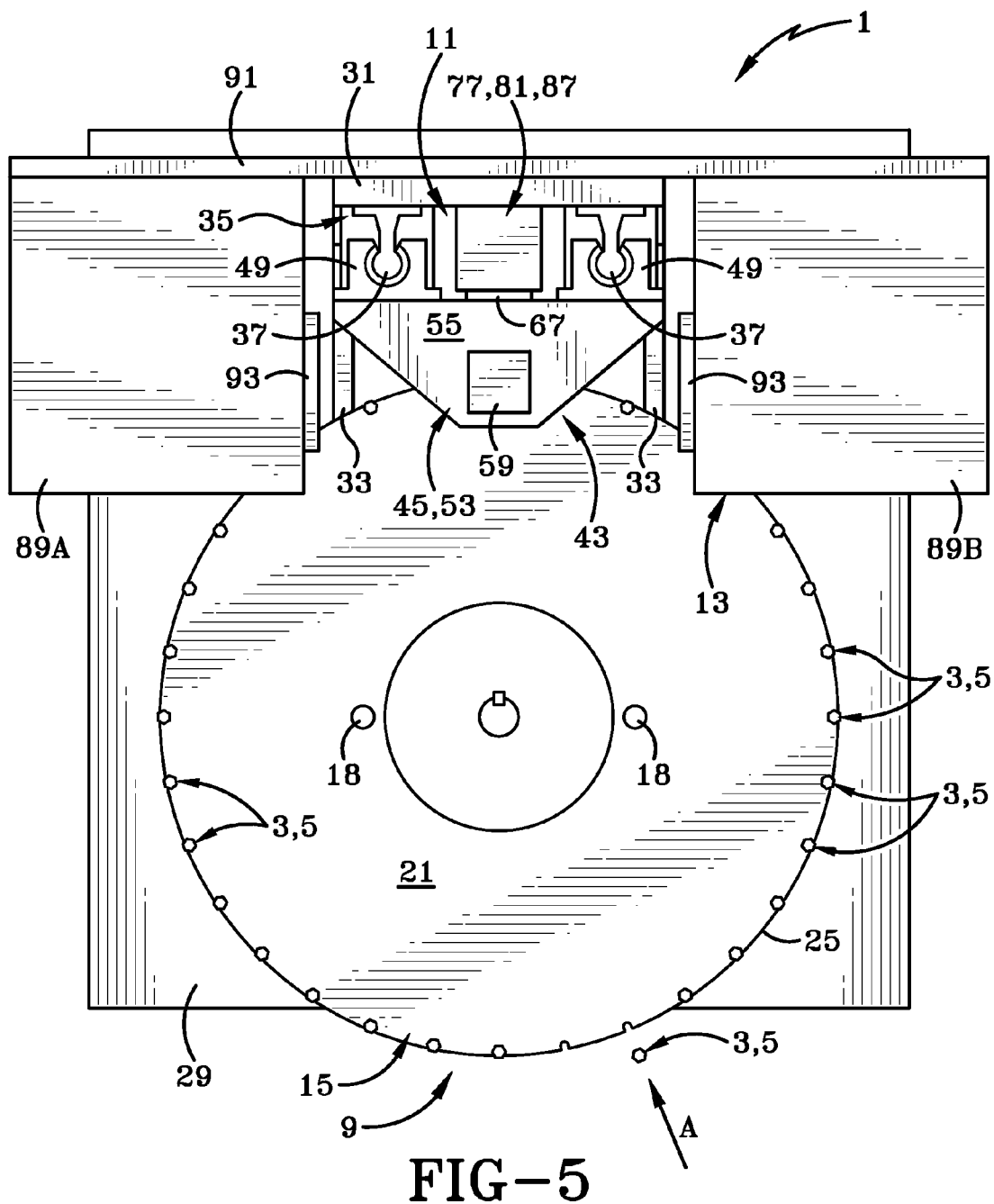
FIG. 5 is a top view thereof with a plurality of bolts engaged with a plate of the indexer assembly.
Figure 8:
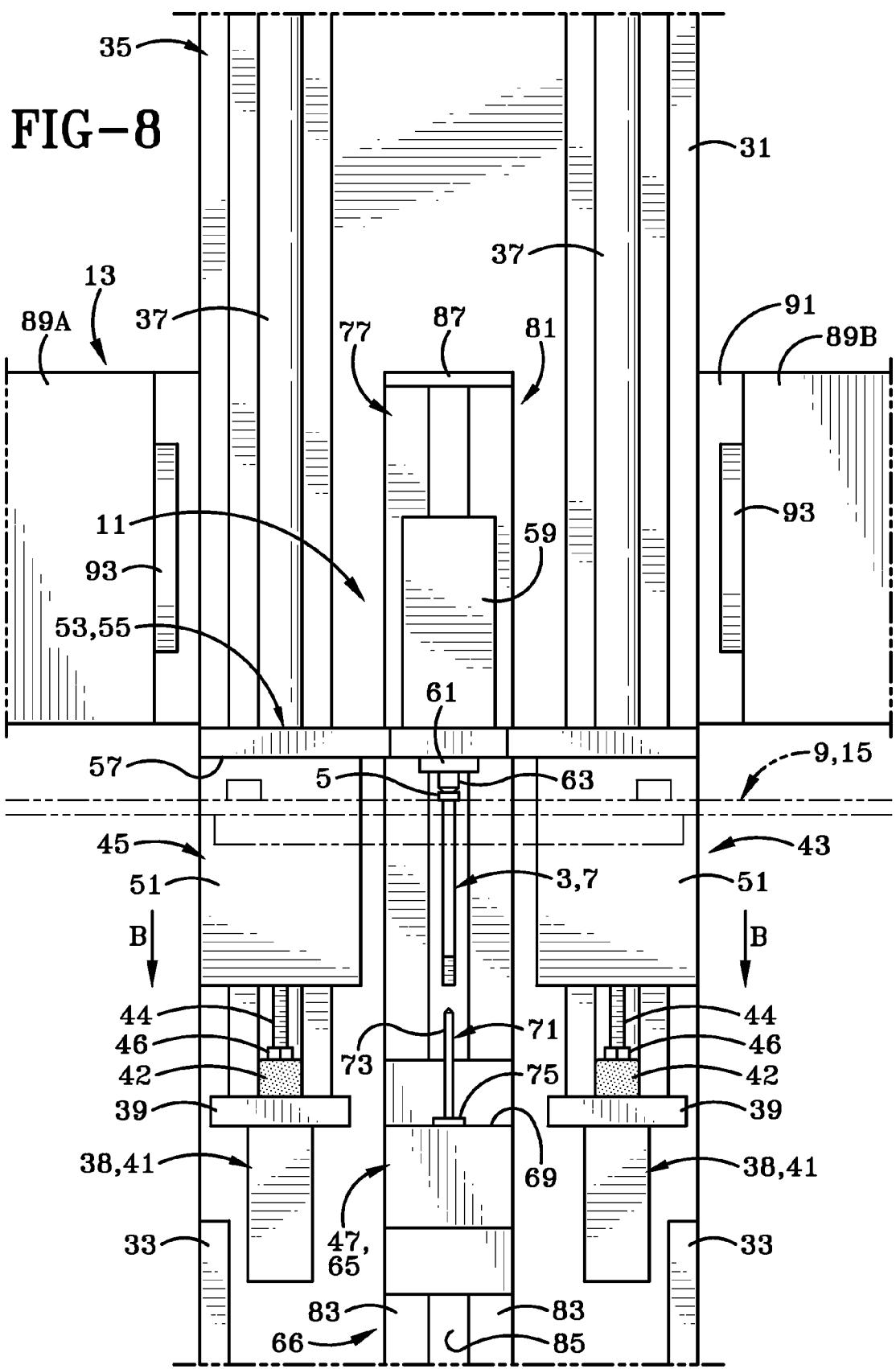
FIG. 8 is a similar view thereof with a first portion of a clamp of the clamp assembly moving in a downward direction.
Figure 10:
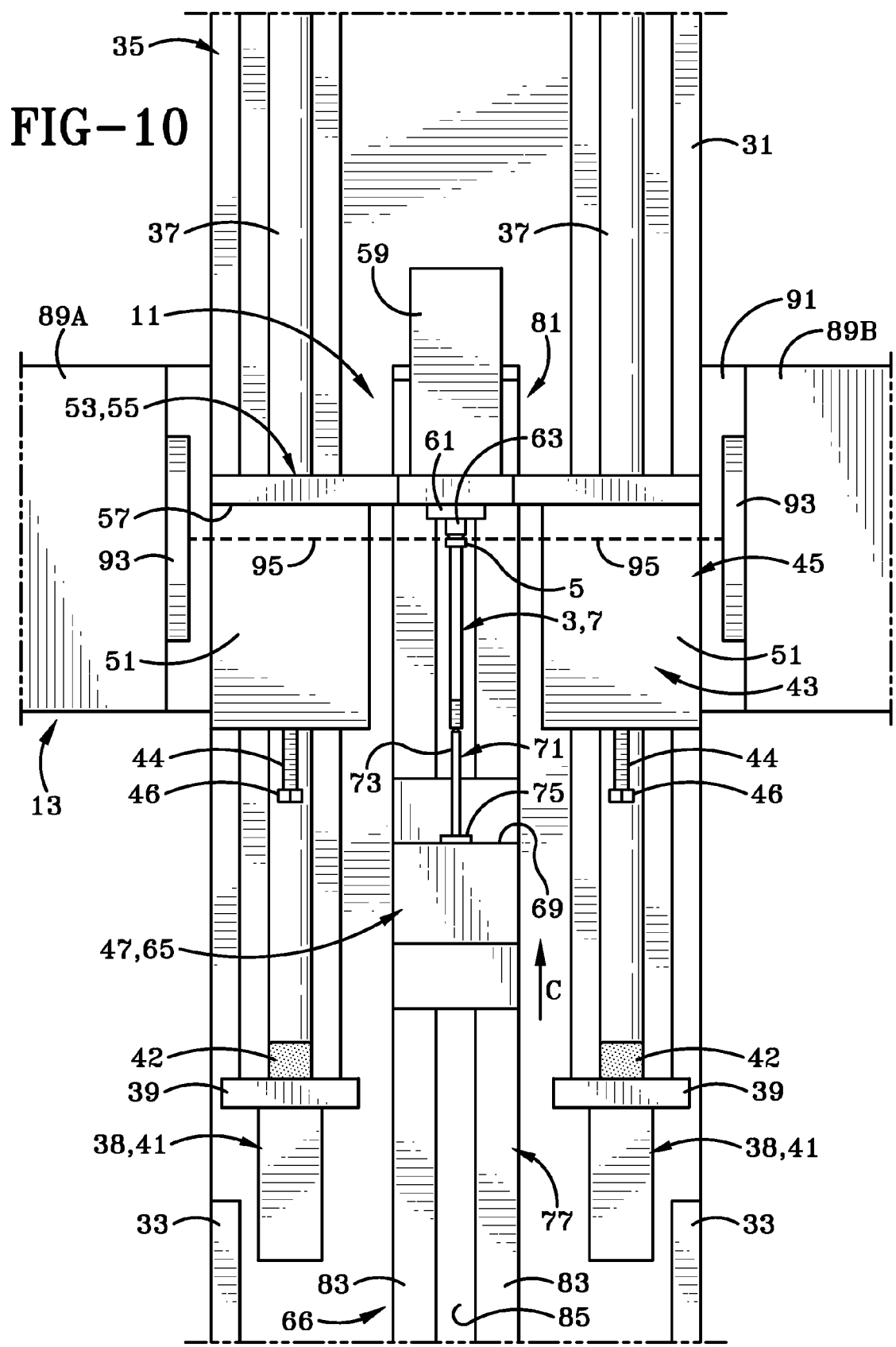
FIG. 10 is a similar view thereof with the first portion and the second portion of the clamp moving in the upward direction to move the bolt past a camera.
Figure 13:
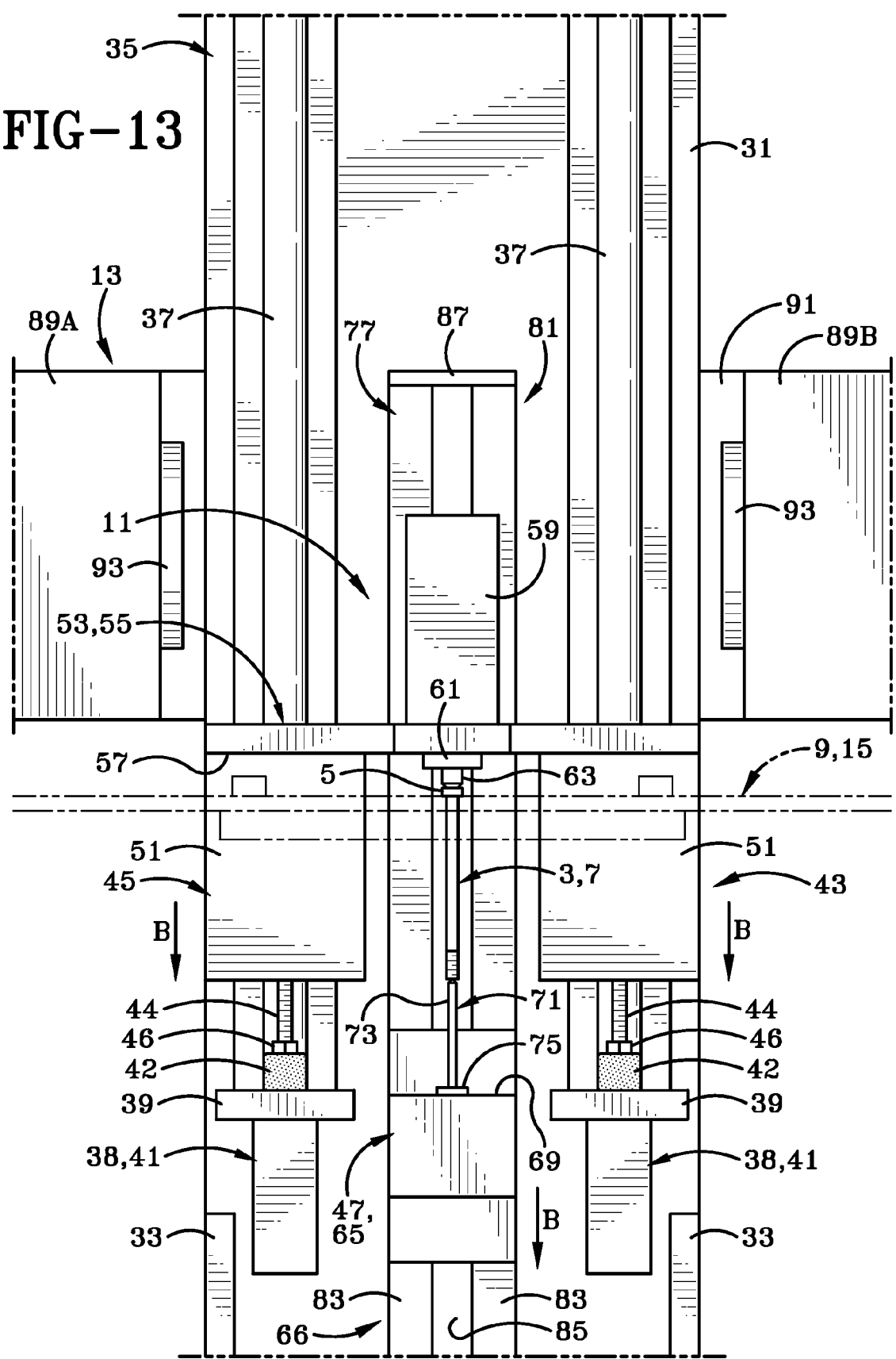
FIG. 13 is a similar view thereof with the first portion and the second portion of the clamp moved in the downward direction.
Figure 14:
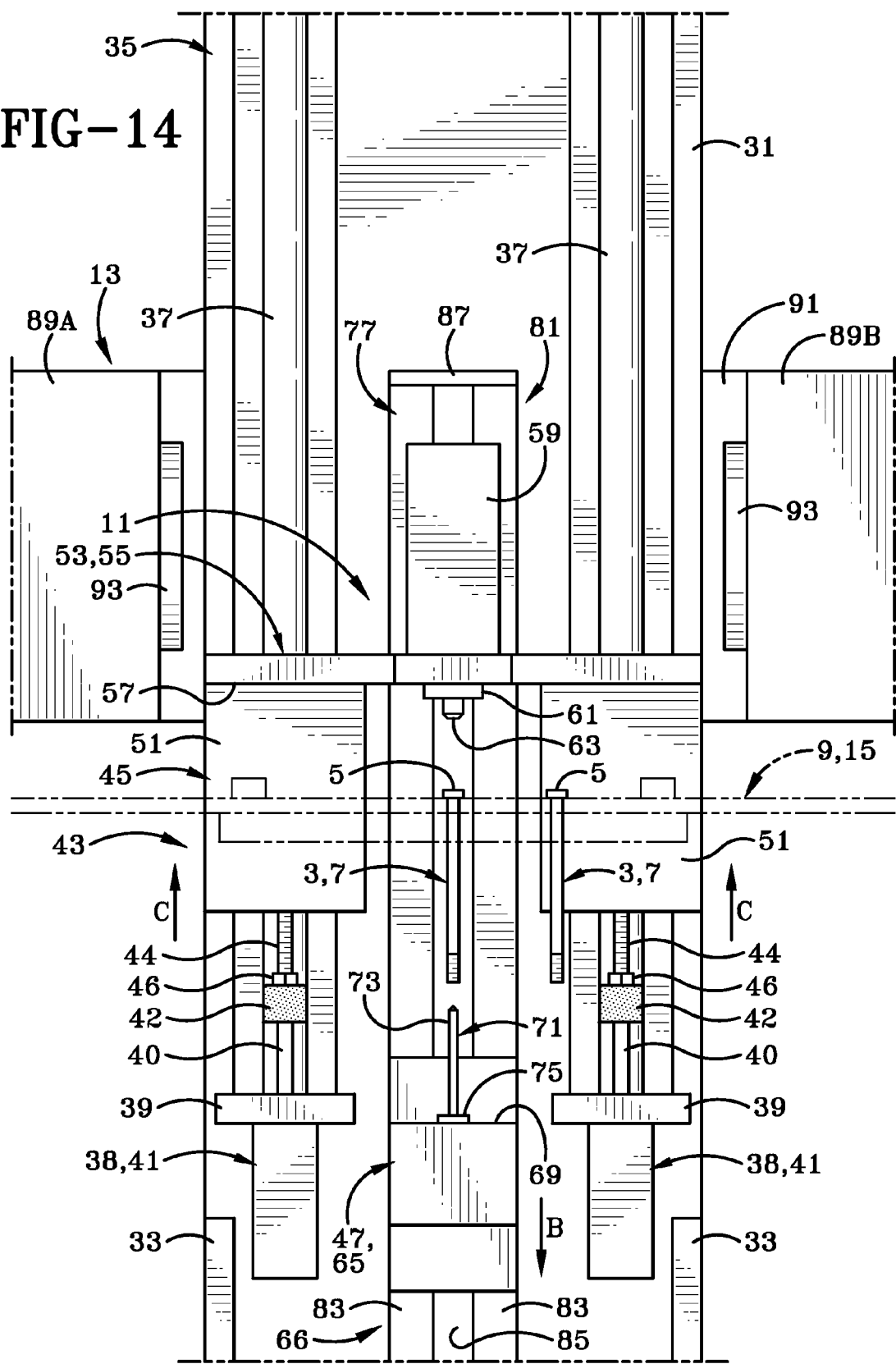
FIG. 14 is a similar view thereof with the first portion of the clamp moving in the upward direction and the second portion of the clamp moving in the downward direction to disengage the clamp from the bolt.

As shown in FIGS. 4 and 7, a threaded rod 44 terminating in a nut 46 extends from spacer 51 towards housing 41 and generally aligned with piston rod 40. Piston rod 40 is actuated by a control system (not shown) which hydraulically or pneumatically moves piston (not shown) inside cylinder (not shown) disposed in housing 41. As shown in FIG. 14, piston rod 40 pushes outwardly away from shelf 39 such that bumper 42 abuts nut 46 of threaded rod 44, thereby pushing threaded rod 44 and first portion 45. This moves the entire first portion 45 upwardly along track 35 in a first direction. First direction is shown in FIG. 14 as Arrow C. As shown in FIG. 8, to move in the opposite, or downward, direction along track 35, the control system simply releases pressure on piston (not shown) which allows the overall weight of first portion 45 to move in a second direction towards housing 41 due to gravity and the overall weight of first portion 45, which is increased by weight 59. Second direction is shown in FIGS. 8 and 13 as Arrow B. As shown in FIG. 10, piston rod 40 may retract into housing 41 beyond the length of threaded rod 44, thereby allowing nut 46 and bumper 42 to separate. By rotating nut 46, the length of threaded rod 44 extending from space 51 may be customized to control how far in the second direction first portion 45 may extend. As shown in FIG. 14, the length of threaded rod 44 should be set to provide enough room for piston rod 40 to lift first portion 45 off bolt 3 as required. When a new plurality of bolts 3 are positioned in slots 27, nut 46 and threaded rod 44 is rotated to account for the new length of the new plurality of bolts 3.

As shown in FIGS. 1A and 2A, second portion 47 includes a base 65 secured to a carriage 67 of a linear slide system 66. Base 65 extends outwardly from carriage 67 to include a top surface 69. A pin 71 having a shaft 73 extending from a puck 75 is secured to top surface 69 of base 65. Carriage 67 rides on a track 77 of linear slide system 66 extending from a first end 79 proximate plate 29 to a second end 81. Track 77 is comprised of two spaced apart rails 83 defining a channel 85 therebetween. Carriage 67 complementarily fits to track 77 to ride along rails 83 and channel 85 from first end 79 to second end 81. Linear slide system 66 may also include a cap 87 disposed proximate second end 81 to provide a stopper and prevent carriage 67 from riding past the end of track 77. Linear slide system 66 includes a servomotor (not shown) for rotating a movement mechanism to move carriage 67 along track 77 in either the first direction or the second direction. In the preferred embodiment, the movement mechanism is embodied in a stainless steel lead rolled drive screw which is disposed primarily in channel 85 and extends through a receptacle area (not shown) in carriage 67. The rotation of the drive screw by servomotor moves carriage 67 along the drive screw, either upwards or downwards depending on the axial rotation direction of the drive screw. Linear slide system 66 further includes an encoder (not shown) for sensing movement of carriage 67 and providing feedback to servomotor regarding the movement, speed, and force of carriage 67. Linear slide system 66 is actuated and controlled by control system to move carriage 67 in the first direction or in the second direction as needed.

Linear slide system 66 of second portion 47 is connected or linked to camera system 13 through control system. As shown in FIGS. 1 and 2, camera system 13 includes a pair of cameras 89, referred to individually as 89A and 89B. Each camera 89 is mounted to a wall 91 secured to back wall 31. Each camera 89 includes a lens 93, wherein lenses 93 are generally directed towards one another with track 35 and track 77 disposed intermediate camera 89A and camera 89B. This orientation of lenses 93 of camera 89A and camera 89B facilitates moving bolt 3 past each camera 89 when bolt 3 is moved by clamp 43.

In the preferred embodiment, cameras 89 are line scan cameras. Line scan cameras have a single row of pixel sensors instead of a matrix of pixel sensors. Traditionally, maintaining consistent lighting over large areas for photographing is difficult. Line scan cameras simply require even illumination across the "line" currently being captured by the camera. This makes possible extremely sharp and detailed pictures of objects that pass by the camera at high speed. As such, cameras 89 may include a light (not shown) directed to where the clamp 43 moves bolt 3 along a path through a scanning line 95 (FIG. 10) of the associated camera 89. Cameras 89 scan bolt 3 as it moves past and along the path, acquiring a plurality of a single row of pixels. Camera system 13 then buffers the plurality of single rows of pixels for later retrieval. When the scanning is completed, camera system 13 retrieves and joins the plurality of single rows of pixels to form a detailed and complete image of bolt 3. Camera system 13 thereafter uses software logic or logic circuitry to process and inspect the image and determine whether any unacceptable imperfections exist in bolt 3.

Inasmuch as camera system 13 is connected to linear slide system 66 through control system, linear slide system 66 is configured to send signals to camera system 13. Camera system 13 is configured trigger cameras 89 to acquire a single row of pixels when a signal is received from linear slide system 66. Accordingly, linear slide system 66 is configured to generate a signal for every unit of distance the encoder measures carriage 67 or any other element of linear slide system 66 moving in the first direction. The unit of distance is configurable by the user and it preferably less than the height of a pixel to ensure every portion of bolt 3 is captured by cameras 89. In one embodiment, the unit of distance is 0.000007 inches. Thus, for every 0.000007 inches carriage 67 travels, a signal is generated by linear slide system 66 and sent to camera system 13. Upon receipt of each signal, camera system 13 triggers cameras 89 to acquire a new single row of pixels for use in forming the overall complete image of bolt 3.

In operation, a method for inspecting a part using apparatus 1 is shown in FIGS. 1-15 and referred to generally herein as method 101. Method 101 begins with apparatus 1 in the position shown in FIG. 4, with plate 15 free of the plurality of bolts 3 and piston rod 40 fully extended. As shown in FIG. 5, a user then manually places the plurality of bolts 3 into slots 27 in the direction of Arrow A. Slots 27 are defined such that head 5 of bolt 3 does not pass therethrough, while shaft 7 of bolt 3 extends through slots 27. In this orientation, bolt 3 is releasably held within slot 27 by way of head 5 abutting upper surface 21 of plate 15. As shown in FIG. 6, inasmuch as slots 27 surround the perimeter of plate 15, when the plurality of bolts 3 are placed within slots 27, bolts 3 are generally spaced evenly around the perimeter of plate 15 and held therein for inspection.

As shown in FIG. 7, method 101 includes the step of disposing bolt 3 between first portion 45 and second portion 47 in general and between pressure head 63 and pin 71 specifically. In this step, indexer assembly 9 rotates plate 15 in the direction of Arrow D (FIG. 15) to index or align one of the plurality of bolts 3 between pressure head 63 and pin 71. Upon proper alignment, piston assembly 38 releases the pneumatic or hydraulic pressure on the piston connected to piston rod 40. This releases upward pressure on bumper 42 specifically and first portion 45 in general. First portion 45 is free to retract downwardly due to gravity in the direction of Arrow B which results in pressure head 63 resting on head 5 of bolt 3. Note that weight 59 is directly vertically above pressure head 63, which increases the overall gravitational pressure and force on head 5 to firmly abut head 5 with upper surface 21.

Figure 9:
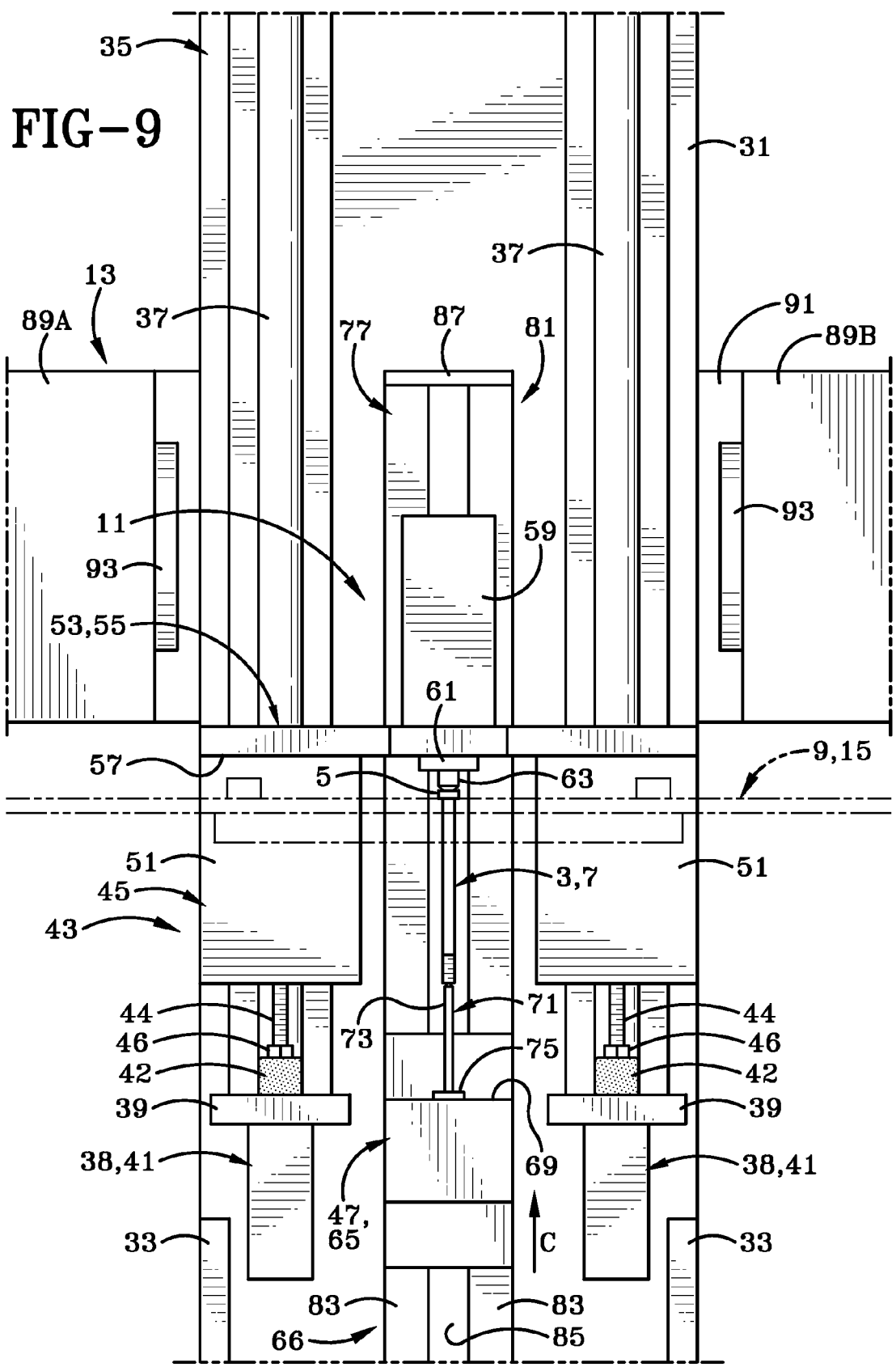
FIG. 9 is a similar view thereof with a second portion of the clamp moving in an upward direction.

As shown in FIG. 9, after pressure head 63 is firmly abutting head 5 of bolt 3, the control system actuates second portion 47 to move in the direction of Arrow C. Inasmuch as shaft 7 is directly in line with pin 71 as second portion 47 rises in the direction of Arrow C, pin 71 contacts the end of shaft 7. Internally, to raise second portion 47 in the direction of Arrow C, linear slide 66 acts to move carriage 67 in the direction of Arrow C. Inasmuch as base 65 is secured to carriage 67, the movement of carriage 67 moves base 65. At this stage of method 101, first portion 45 is resting upon bolt 3 simply due to gravity acting on first portion 45. Other than gravity, there are no other elements of apparatus 1 acting upon first portion 45. As second portion 47 moves in the direction of Arrow C, linear slide 66 is configured such that the servomotor internal to linear slide 66 is sufficient to overcome the downward gravitational pressure on bolt 3 from first portion 45 and move the entire combination of first portion 45, bolt 3, and second portion 47 in the direction of Arrow C. Stated another way, the upward pressure on bolt 3 from second portion 47 is greater than the downward pressure on bolt 3 from first portion 45. Thus, the entire combination of first portion 45, bolt 3, and second portion 47 move in accordance with the greater pressure of second portion 47.

As shown in FIG. 10, bolt 3 is clamped between first portion 45 and second portion 47, and the entire combination of first portion 45, bolt 3, and second portion 47 is moving in the direction of Arrow C. Note that bumpers 42 remain proximate shelf 39 as second portion 47 pushes first portion in the first direction. Threaded rod 44 is secured to spacer 51 while bumper 42 is secured to piston rod 40. While threaded rod 44 and bumper 42 are in abutting contact at various stages of method 101, threaded rod 44 and bumper 42 are not connected or secured together and are free to separate as required by method 101.

As shown in FIG. 10, the movement of carriage 67 is sensed by the encoder connected to the servomotor of linear slide 66. As such, the encoder signals cameras 89 to begin acquiring a plurality of single rows of pixels of bolt 3 along scanning line 95. As shown in FIG. 10, camera 89A acquires a plurality of single rows of pictures of a first side of bolt 3, while camera 89B acquires a plurality of single rows of pixels of a second side of bolt 3. Thus, both sides of bolt 3, and correspondingly all of bolt 3 are scanned by cameras 89A and 89B working in conjunction. Any area on bolt 3 not available for scanning by camera 89A is available for scanning by camera 89B, and conversely, any area not scannable by camera 89B is necessarily scannable by camera 89A.

Figure 11:
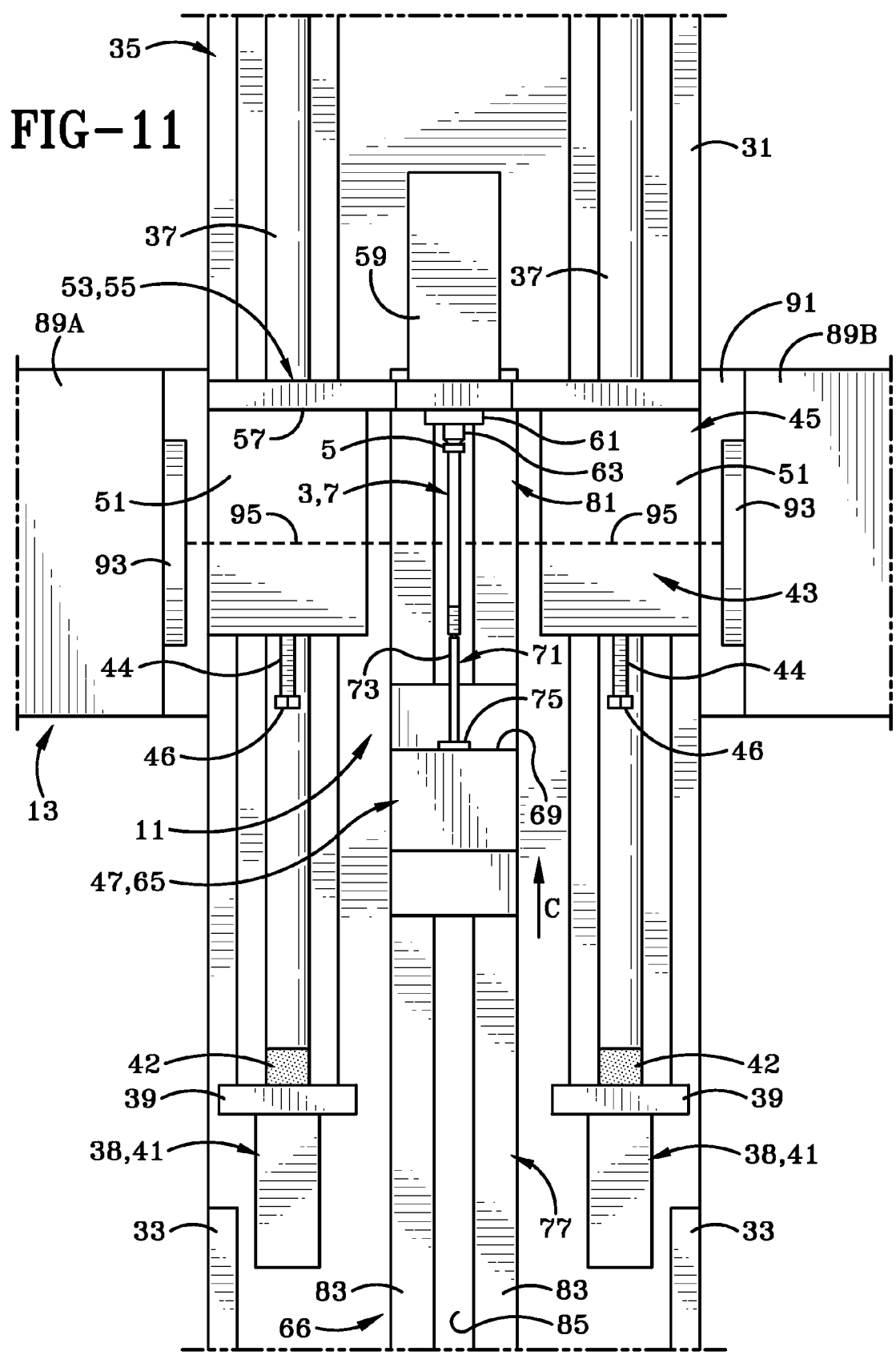
FIG. 11 is a similar view thereof with the first portion and the second portion of the clamp moving in the upward direction to move the bolt further past the camera.
Figure 12:
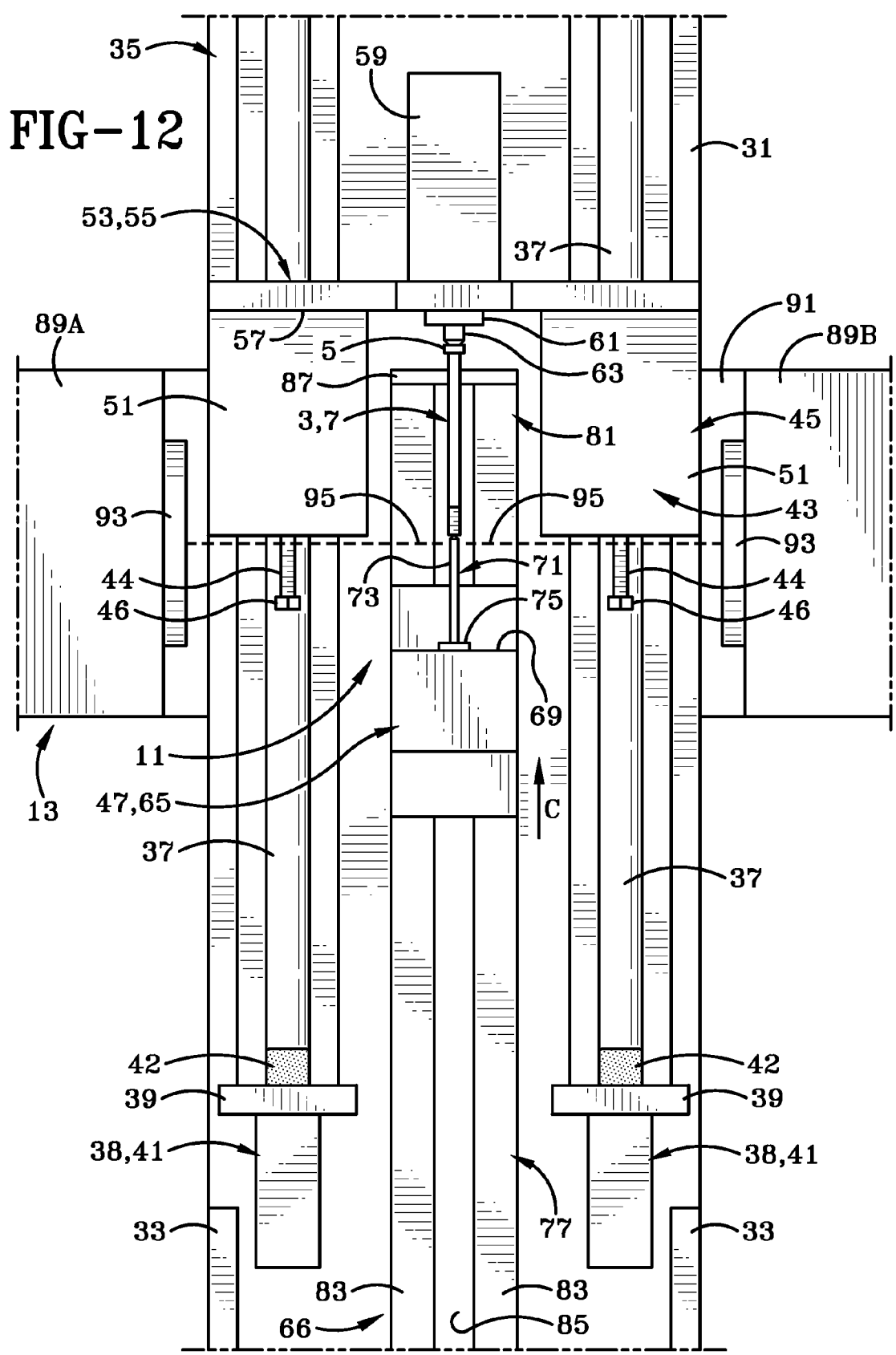
FIG. 12 is a similar view thereof with the bolt moved entirely past the camera.

As shown in FIG. 10, scanning line 95 encounters head 5 of bolt first as clamp 43 moves bolt 3 along the path and in the direction of Arrow C. As shown in FIG. 11, clamp 43 continues to move bolt 3 in the direction of Arrow C allowing cameras 89 to scan shaft 7 of bolt 3 as it passes through scanning line 95. Pin 71 passes into slot 27 and is disposed therein at this stage to enable bolt 3 to move along the path and in the first direction. Finally, as shown in FIG. 12, clamp 43 moves the remaining portion of bolt 3 past scanning line 95 to complete the overall scanning of bolt 3. During the entire scanning process, each camera 89A and 89B scan bolt 3 from their respective directions and acquire a plurality of single rows of pixels of bolt 3. As discussed previously, cameras 89 are actuated or triggered to acquire a single row of pixels by the encoder of linear slide 66. The encoder generates a signal for every unit of distance second portion 47 moves in the first direction, which is the direction of Arrow C. The user may configure the unit of distance via the control system. For example, the unit of distance may be 0.000007 inches of travel. Thus, for every 0.000007 inches that second portion 47 or any portion of linear slide 66 travels, the encoder generates a signal and sends the signal to cameras 89. Upon receipt of this signal, cameras 89 acquire a single row of pixels of the area of bolt 3 currently disposed in scanning line 95. Upon completion of scanning the entire bolt 3 as it moves along the path, the underlying software logic or logic circuitry joins the acquired single rows of pixels to form a complete image of bolt 3. This software logic or logic circuitry then analyzes this image to inspect bolt 3 and determine whether bolt 3 conforms to all material and design requirements.

As shown in FIG. 13, upon completion of scanning, linear slide 66 actuates carriage 67 to move in the direction of Arrow B. Inasmuch as first portion 45 is resting on bolt 3, which is resting on second portion 47, this moves first portion 45, bolt 3, and second portion 47 in the second direction, generally in the direction of Arrow B. Threaded rods 44 move in the direction of Arrow B until each threaded rod 44 abuts bumper 42. This halts the downward direction of first portion 45 as bumpers 42 firmly prevent first portion 45 from traveling further in the direction of Arrow B. Inasmuch as second portion 47 is independently movable with respect to first portion 45, second portion 47 continues to travel in the direction of Arrow B. As shown in FIG. 14, this withdraws pin 71 from slot 27 and releases the abutting relationship between pin 71 and bolt 3 as second portion 47 moves in the direction of Arrow B. Finally, piston assembly 38 thereafter increases internal pneumatic or hydraulic pressure on the piston disposed in the cylinder contained within housing 41. This moves piston rod 40 in the direction of Arrow C which presses bumper 42 upon threaded rod 44 to move the entire first portion 45 in the direction of Arrow C, thereby releasing pressure head 63 from head 5 of bolt 3. As shown in FIG. 5, at this stage of method 101, bolt 3 has now been inspected by apparatus 1 and plate 15 is free to rotate in the direction of Arrow D to move the inspected bolt 3 away from the alignment between first portion 45 and second portion 47. This further rotates a new bolt 3 into position between first portion 45 and second portion 47 as indexer assembly 9 is configured to index the next bolt 3 in succession for automatic scanning of each bolt 3 in the plurality. Method 101 continues scanning each bolt 3 in the plurality in accordance with the described steps until each bolt 3 in the plurality is scanned and inspected. Method 101 may include an alarm or notification mechanism for notifying the user when a particular bolt 3 fails the inspection. This notification may include halting the overall method 101 until the user removes the problem bolt 3. Alternatively, apparatus 1 and method 101 may include a mechanism for automatically rejecting the problem bolt 3 by including a mechanism for moving the problem bolt 3 out of its respective slot 27 automatically which would thereby allow the problem bolt 3 to fall on the ground or plate 29 for later discarding.

"Logic," "logic circuitry," or "logic circuit," as used herein, includes but is not limited to hardware, firmware, software and/or combinations of each to perform a function(s) or an action(s), and/or to cause a function or action from another logic, method, and/or system. For example, based on a desired application or needs, logic may include a software controlled microprocessor, discrete logic like a processor (e.g., microprocessor), an application specific integrated circuit (ASIC), a programmed logic device, a memory device containing instructions, or the like. Logic may include one or more gates, combinations of gates, or other circuit components. Logic may also be fully embodied as software. Where multiple logics are described, it may be possible to incorporate the multiple logics into one physical logic. Similarly, where a single logic is described, it may be possible to distribute that single logic between multiple physical logics.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

In the foregoing description, certain terms have been used for brevity, clearness, and understanding. No unnecessary limitations are to be implied therefrom beyond the requirement of the prior art because such terms are used for descriptive purposes and are intended to be broadly construed.

While the present invention has been described in connection with the preferred embodiments of the various figures, it is to be understood that other similar embodiments may be used or modifications and additions may be made to the described embodiment for performing the same function of the present invention without deviating there from. Therefore, the present invention should not be limited to any single embodiment, but rather construed in breadth and scope in accordance with the recitation of the appended claims.

What is claimed is:

1. An apparatus adapted to inspect a part, the apparatus comprising:
 a clamp having a first portion and a second portion, wherein the first portion and the second portion are independently movable to clamp the part therebetween and move the part along a path;

a first camera, wherein the first camera is configured to capture a first image of the part as the clamp moves the part along the path; and a plate defining a slot for receiving the part therein, wherein the plate is rotatable to selectively dispose the part between the first portion and the second portion and remove the part from between the first portion and the second portion; and a piston assembly, and wherein the piston assembly moves the first portion.

2. The apparatus of claim 1, wherein the piston assembly includes a piston movably disposed in a cylinder and a piston rod connected to the piston; and wherein the piston rod moves the first portion.

3. The apparatus of claim 1, further comprising:

a linear slide assembly; and wherein the linear slide moves the second portion.

4. The apparatus of claim 3, wherein the linear slide assembly includes a carriage movable along a pair of rails, and wherein the second portion is secured to the carriage.

5. The apparatus of claim 4, wherein the linear slide assembly further includes a servomotor and a drive screw coupled with the carriage, and wherein the servomotor rotates the drive screw to move the carriage and second portion.

6. The apparatus of claim 5, wherein the linear slide assembly further includes an encoder coupled with the first camera, wherein the encoder is configured to measure the movement of the carriage and generate a signal for every predefined unit of distance the carriage moves.

7. The apparatus of claim 6, wherein the camera is configured to acquire a single row of pixels of the part upon receipt of a signal from the encoder, and wherein the first image includes the single row of pixels.

8. An apparatus adapted to inspect a part, the apparatus comprising:

a clamp having a first portion and a second portion, wherein the first portion and the second portion are independently movable to clamp the part therebetween and move the part along a path;

a first camera, wherein the first camera is configured to capture a first image of the part as the clamp moves the part along the path;

a plate defining a slot for receiving the part therein, wherein the plate is rotatable to selectively dispose the part between the first portion and the second portion and remove the part from between the first portion and the second portion;

a second camera configured to capture a second image of a second side of the part as the clamp moves the part along the path;

wherein the first camera is configured to capture the first image of a first side of the part as the clamp moves the part along the path; and wherein the first side and the second side are generally opposite sides of the path.

9. A method for inspecting parts, the method comprising the steps of:

clamping a part to be inspected;

moving the clamp and the part past a camera;

using the camera to form an image of the part;

analyzing the image to inspect the part;

moving a first portion of the clamp to apply pressure to a first end of the part;

moving a second portion of the clamp in a first direction to apply pressure to a second end of the part to clamp the part to be inspected; and further comprising the step of overcoming the pressure of the first portion of the clamp with the pressure of the second portion of the clamp to thereby move the first portion, the part, and the second portion past the camera in the first direction.

10. The method of claim 9, further comprising the steps of:

generating a signal;

sending the signal to the camera; and configuring the camera to acquire a single row of pixels of the part in response to receiving the signal.

11. The method of claim 10, further comprising the step of linking the generating of the signal with the movement of one of the first portion and the second portion.

12. The method of claim 11, further comprising the steps of:

defining a unit of distance;

generating a signal for every unit of distance the one of the first portion and second portion moves in the first direction;

sending the signal to the camera; and joining the acquired single rows of pixels to form the image.

13. The method of claim 12, further comprising the steps of:

using a servomotor having an encoder to move the one of the first portion and the second portion;

measuring the linear distance the one of the first portion and the second portion moves via the encoder; and generating the signal for every unit of distance the encoder measures the one of the first portion and the second portion moving in the first direction.

14. The method of claim 9, further comprising the steps of:

manually inserting the part in a slot defined by a plate; and rotating the plate to dispose the part between the first portion of the clamp and the second portion of the clamp.

15. The method of claim 14, further comprising the step of extending a pin of the second portion through the slot to move the part past the camera in the first direction.

16. The method of claim 9, further comprising the step of increasing a pressure in a piston assembly to move the first portion of the clamp in the first direction.

17. The method of claim 9, further comprising the step of applying pressure to the first end of the part by way of gravity acting on the first portion.

* * * * *